United States Patent
Du et al.

(10) Patent No.: US 6,439,229 B1
(45) Date of Patent: Aug. 27, 2002

(54) PRESSURE SUPPORT VENTILATION CONTROL SYSTEM AND METHOD

(75) Inventors: Hong-Lin Du, Santa Ana, CA (US); Marcelo B. P. Amato, Jaguare (BR); Yoshitsugu Yamada, Tokyo (JP); Bich N. Nguyen, Corona, CA (US)

(73) Assignee: Newport Medical Instruments, Inc., Costa Mesa, CA (US)

( * ) Notice: Subject to any disclaimer, the term of this patent is extended or adjusted under 35 U.S.C. 154(b) by 93 days.

(21) Appl. No.: 09/634,513

(22) Filed: Aug. 8, 2000

(51) Int. Cl.[7] ............................................. A61M 16/00
(52) U.S. Cl. ............................. 128/204.23; 128/204.21; 128/204.26
(58) Field of Search ....................... 128/204.18, 204.21, 128/204.23, 204.26

(56) References Cited

U.S. PATENT DOCUMENTS

| | | | | |
|---|---|---|---|---|
| 4,323,064 A | * | 4/1982 | Hoenig et al. | 128/204.21 |
| 5,107,830 A | * | 4/1992 | Younes | 128/204.23 |
| 5,161,525 A | | 11/1992 | Kimm et al. | |
| 5,316,009 A | * | 5/1994 | Yamada | 128/204.23 |
| 5,323,772 A | | 6/1994 | Linden et al. | |
| 5,373,842 A | | 12/1994 | Olsson et al. | |
| 5,383,449 A | | 1/1995 | Forare et al. | |
| 5,390,666 A | * | 2/1995 | Kimm et al. | 128/204.23 |
| 5,540,219 A | | 7/1996 | MechlenbUrg et al. | |
| 5,540,220 A | * | 7/1996 | Gropper et al. | 128/204.23 |
| 5,546,933 A | | 8/1996 | Rapoport et al. | |
| 5,582,163 A | * | 12/1996 | Bonassa | 128/204.23 |
| 5,647,351 A | * | 7/1997 | Weismann et al. | 128/204.21 |
| 5,720,278 A | | 2/1998 | Lachmann et al. | |
| 5,797,393 A | * | 8/1998 | Kohl | 128/204.23 |
| 5,884,622 A | * | 3/1999 | Younes | 128/204.23 |
| 5,931,162 A | * | 8/1999 | Christian | 128/204.23 |
| 5,937,853 A | | 8/1999 | Ström | |
| 6,029,664 A | * | 2/2000 | Zdrojkowski et al. | 128/204.23 |
| 6,213,119 B1 | * | 4/2001 | Brydon et al. | 128/204.23 |
| 6,305,374 B1 | * | 10/2001 | Zdrojkowski et al. | 128/204.23 |
| 6,318,365 B1 | * | 11/2001 | Vogele et al. | 128/204.23 |

OTHER PUBLICATIONS

Martin J. Tobin, M.D., *Principles and Practice of Mechanical Ventilation*, book, 1994, 1233–1259, McGraw–Hill, Inc., United States.

Amal Jubran et al., *Variability of Patient–Ventilator Interaction with Pressure Support Ventilation in Patients wth Chronic Obstructive Pulmonary Disease*, 1995, 129–136, vol. 152.

800 Ventilator Series, 840 Infant—Pediatric—Adult.

Yoshitsugu Yamada, M.D. et al., *Effects of Different Pressure Support Termination on Patient–Ventilator Synchrony*, Respiratory Care book, Dec. 1998, 1048–1057, vol. 43.

* cited by examiner

*Primary Examiner*—Aaron J. Lewis
(74) *Attorney, Agent, or Firm*—Brown, Martin, Haller & McClain, LLP

(57) ABSTRACT

A system and method of controlling the termination of the inhalation phase in a pressure support ventilation system is disclosed, in which an expiratory trigger sensitivity, or ratio of inspiratory flow rate to peak inspiratory flow rate at which the inspiration phase is terminated, is varied in proportion to variations in a calculated respiratory time constant. The system includes sensors for monitoring pressure and flow of gas during each breath, and, based on the sensor outputs, calculates the respiratory time constant for one breath or a series of breaths. The expiratory trigger sensitivity is automatically increased with increasing patient respiratory time constant, providing a closed loop control of expiratory trigger sensitivity. The expiratory trigger sensitivity may also be varied in response to changes in supra-plateau pressure.

15 Claims, 3 Drawing Sheets

PRESSURE SUPPORT VENTILATION CONTROL SYSTEM AND METHOD

BACKGROUND OF THE INVENTION

The present invention relates to a breathing apparatus or ventilator system for supplying gases to a living being such as a human or animal patient to assist the patient in breathing, and is particularly concerned with a control system and method for controlling switching of the ventilator from gas delivery (inhalation) to gas removal (expiration).

There are two types of ventilation used to assist breathing in certain patients. One is complete control of breathing, in which the ventilator completely takes over the patient's breathing function. The other partially supports the patient's breathing function, such as pressure support ventilation, or PSV, in which the ventilator simply assists the patient's own breathing function. PSV is generally more comfortable for the patient, as long as the ventilator can be synchronized with the patient's natural breathing effort. However, accurate synchronism of the ventilator with the patient is a long-standing problem in PSV.

In known pressure support ventilators, a breathing apparatus is connected to a patient through an inspiration line, for supplying gas to the patient, and an expiratory line, for allowing removal of expired gases from the patient. A valve in each line controls the inspiration phase and the expiration phase of the breathing cycle, and the opening and closing of each valve are controlled by a control unit based on a desired pressure target level. Typically, during pressure support ventilation, the breathing apparatus starts to deliver gases to the patient when a spontaneous breathing effort is detected by a pressure gauge or flow sensor. The ventilator flow in inspiration is normally terminated when the inspiratory flow rate decays to a predetermined percentage of the peak inspiratory flow rate, typically between 5% to 25% of the peak inspiratory flow rate. This percentage is commonly known as the termination criterion or the expiratory trigger sensitivity, or ETS. In some cases, the termination of inspiration can be selected manually by the user. In each of these cases, the termination criterion, or ETS, is always a fixed number or percentage, regardless of variations between patients or changes in the condition of an individual patient over time.

Clinical studies have revealed that patients under pressure support ventilation, or PSV, often encounter patient-ventilator asynchrony. In expiratory asynchrony, the termination of ventilator flow occurs either prematurely, before the patient stops his inspiratory effort, or late, after the patient stops his inspiratory effort. In either case, discomfort to the patient is caused. When the termination is late (delayed termination), the patient recruits his expiratory muscles to "fight" against the ventilator flow, increasing expiratory workload. If the termination is too early (premature termination), inspiratory muscle work continues into or even through the ventilator's expiratory phase, resulting in inefficient respiratory muscle work. Although expiratory asynchrony has been of clinical concern for years, no effective solution to this problem has yet been devised. This problem is discussed in the paper entitled "Variability of Patient-Ventilator Interaction with Pressure Support Ventilation in Patients with Chronic Obstructive Pulmonary Disease" by Jubran, A., et al., Am.J.Respir Crit Care Med 152:129–136, 1995. In spite of the known problem of ventilator expiratory asynchrony, most current ventilators still use an arbitrary termination criterion, such as a fixed percentage of the peak flow, in order to terminate the inspiratory flow delivery during PSV. Thus, the Siemens Servo 300 uses 5% of the peak flow as the termination criterion, Siemens Servo 900 and Bird 8400St use 25% of the peak flow, and the Nellcor Puritan Bennett 7200ae uses a flow rate of 5 L/min.

One attempt to avoid the problems of patient-ventilator asynchrony has been to allow the expiratory trigger sensitivity to be adjusted by the doctor or medical personnel. However, this adds significantly to the workload of medical personnel and it has been shown to be difficult to achieve good results based on patient observation at the bedside.

SUMMARY OF THE INVENTION

It is an object of the present invention to provide a new and improved pressure support ventilation control system and method which reduces the risk of patient-ventilator asynchrony.

According to one aspect of the present invention, a pressure support ventilation system is provided, which comprises a source of breathing gases, an inspiration line for connecting the source to a patient, an expiratory line for exhausting gases from the patient, at least one flow sensor for sensing the level of gas flow in the system, a pressure sensor for sensing pressure in the system, and a control unit for controlling supply of gases to a patient in an inspiration cycle, and exhausting gases in the expiratory line in an exhalation cycle, the control unit being connected to the flow sensor and pressure sensor, and calculating, for each breath, a patient respiratory time constant and varying an expiratory trigger sensitivity at which the ventilator switches from inspiration to expiration in response to variations in the patient respiratory time constant, such that the expiratory trigger sensitivity is increased with increases in the respiratory time constant.

Preferably, the control unit or microprocessor is also programmed to calculate the supra-plateau pressure at the end of inhalation, i.e. the pressure above a set target pressure level at the end of inhalation or inspiration, and to adjust the expiratory trigger sensitivity if the supra-plateau pressure is too high.

This system provides automatic closed loop control of the expiratory trigger sensitivity (ETS), i.e. the ratio of inspiratory flow rate to the peak inspiratory flow rate at which the ventilator will switch from a gas delivery (inspiration) phase to a gas removal (expiration) phase. The system uses patient respiratory time constant, which has been found to have an excellent correlation with ventilator synchrony, in order to automatically adjust the expiratory trigger ratio or sensitivity for each breath in a closed-loop manner.

According to another aspect of the present invention, a method of controlling the inhalation phase in a pressure support ventilation system is provided, which comprises the steps of supplying gas to a patient in a ventilator inspiration phase, controlling the termination of the inspiration phase based on a calculated expiratory trigger sensitivity, detecting the flow rate and pressure in the system for each breath, using the detected flow rate and pressure to calculate, for each breath, a new patient respiratory time constant, and determining, for each calculated time constant, a new expiratory trigger ratio, and using the new expiratory trigger sensitivity to control the termination of the inspiration phase in the next breath.

Preferably, a supra-plateau pressure is also calculated for each breath, and this is also used to vary the expiratory trigger sensitivity based on predetermined criteria.

Essentially, the higher the patient respiratory time constant, the higher the expiratory trigger ratio should be in order to achieve a good expiratory synchrony between the patient and ventilator during pressure support ventilation. Also, the relationship between the supra-plateau pressure and the expiratory trigger sensitivity is such that, the higher the supra-plateau pressure, the higher the expiratory trigger sensitivity should be for the next breath. The expiratory trigger sensitivity may be varied based on look-up tables which tabulate the desired relationship between patient respiratory time constant and expiratory trigger sensitivity, and between supra-plateau pressure and expiratory trigger sensitivity.

This closed loop control system and method for automatically varying the expiratory trigger sensitivity (ratio of inspiratory flow rate to the peak inspiratory flow rate at which the ventilator will switch from gas delivery or inspiration to gas removal or expiration) will achieve better patient-ventilator expiratory synchrony than was possible in previous systems with fixed expiratory trigger levels or ratios. This will result in reduced discomfort in patients undergoing pressure support ventilation or PSV.

BRIEF DESCRIPTION OF THE DRAWINGS

The present invention will be better understood from the following detailed description of an exemplary embodiment of the invention, taken in conjunction with the accompanying drawings in which like reference numerals refer to like parts and in which.

DETAILED DESCRIPTION OF THE DRAWINGS

Figure 1:
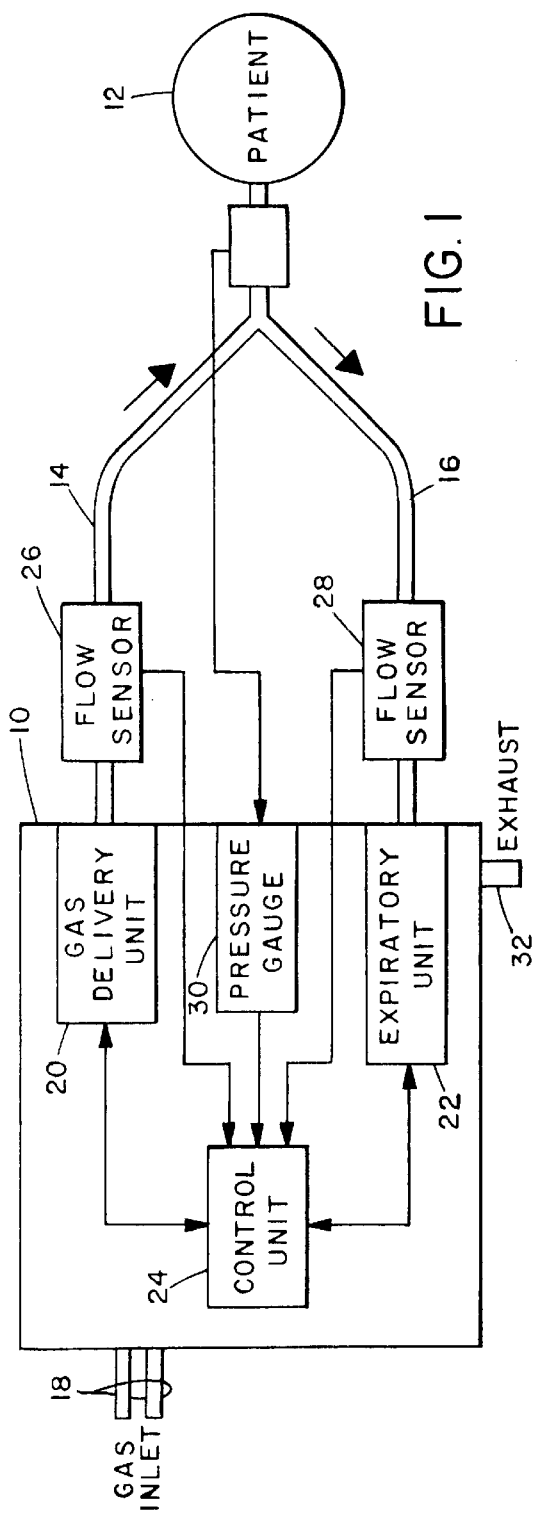
FIG. 1 is a schematic block diagram of a pressure support ventilator according to an exemplary embodiment of the invention.

FIG. 1 of the drawings illustrates a pressure support ventilator or breathing apparatus 10 for connection to a patient 12 via inspiratory line 14 and expiratory line 16. The apparatus is connected to a supply of breathing gases via input 18. The breathing gases may be compressed air, oxygen, or any other suitable gas mixture.

The apparatus 10 includes a gas delivery unit 20 connected to inspiratory line 14, and an expiratory unit 22 connected to the expiratory line. Both units 20 and 22 are connected to a control unit or microprocessor 24 suitably programmed to control the start and end of the inspiratory and expiratory phase of each breath, as described in more detail below. An inspiratory flow sensor 26 is located in inspiratory line 14, and an expiratory or exhalation flow sensor 28 is located in expiratory line 16. Both flow sensors have outputs connected to control unit 24. A pressure sensor or gauge 30 is also provided in the apparatus or in the patient's airway for detecting the patient airway pressure, as is known in the field. The output of pressure sensor 30 is also connected to the control unit. An exhaust port 32 is provided for exhaust of exhalation gases from the patient's lungs.

Figure 3:
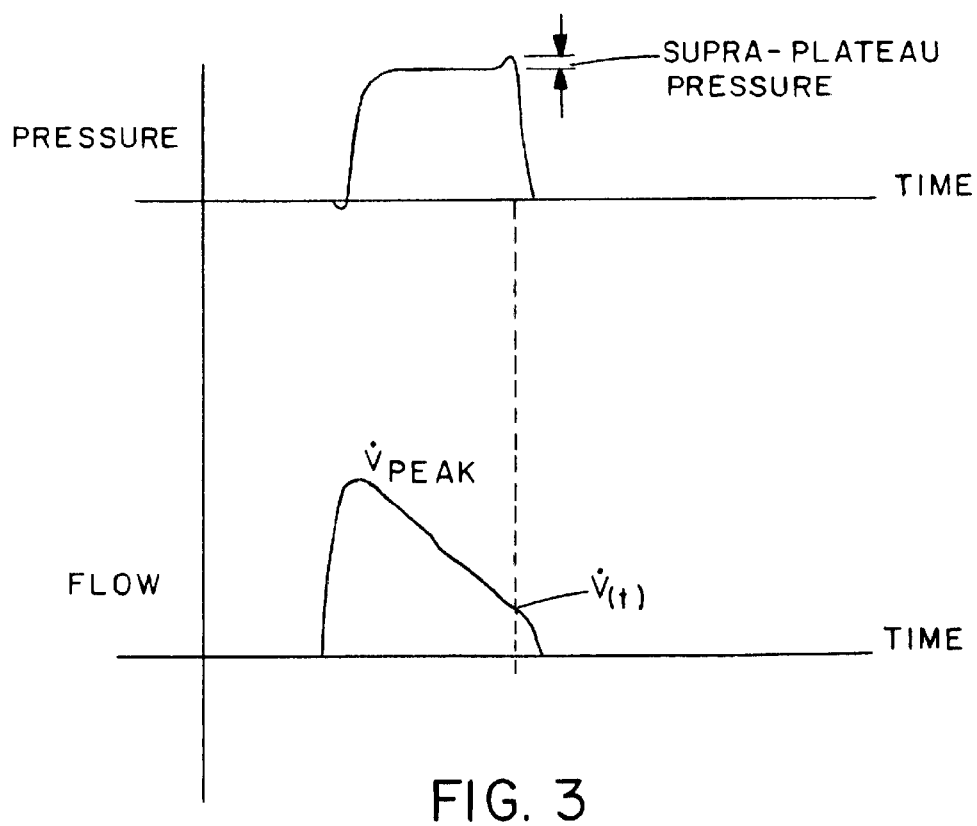
FIG. 3 shows the variation of pressure with time and flow with time in a typical inspiration phase of the ventilator breathing cycle.

During pressure support ventilation (PSV), the breathing apparatus 10 starts to deliver gas to the patient through gas delivery unit 20 when the control unit detects a patient spontaneous effort through pressure gauge 30 or flow sensors 26,28. The gas delivery unit is controlled by the control unit 24 so that the patient airway pressure targets and maintains at a desired pressure level throughout inspiration, as indicated in the upper graph of FIG. 3. During inspiration, the expiratory unit 22 is also controlled by the control unit so that the delivered gases go into the patient's lungs. During inspiration, when the detected flow conditions meet predetermined criteria, i.e. expiratory trigger sensitivity or termination criteria, control unit 24 terminates gas delivery and controls expiratory unit 22 to open the expiratory path to exhaust port 32, so that gases in the patient's lungs can be exhaled out through the exhaust port.

Figure 2:
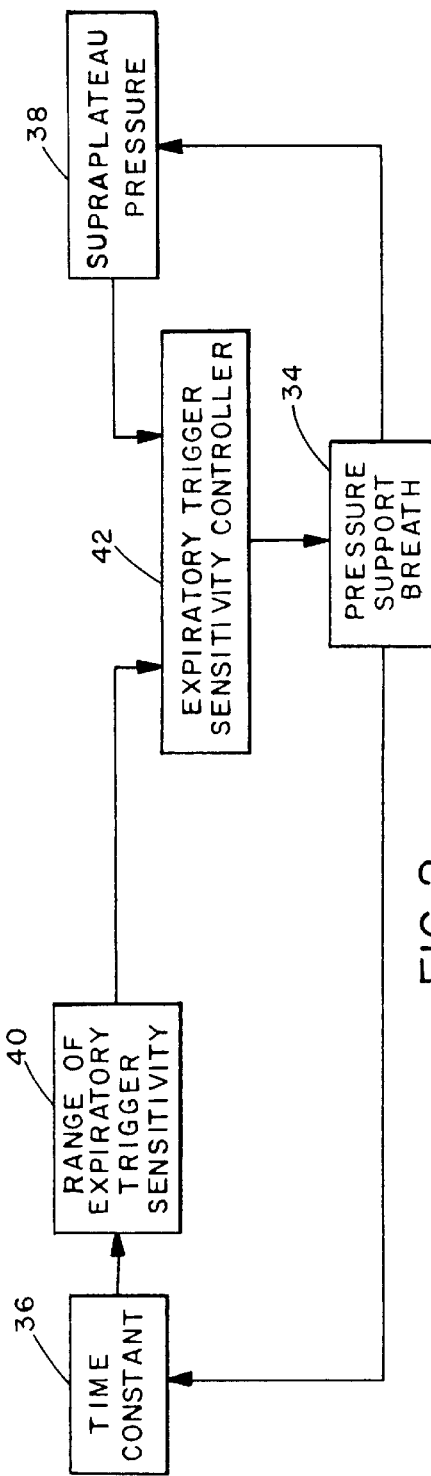
FIG. 2 is a schematic block diagram of a control system and method for controlling switching of the ventilator from inspiration to expiration.

FIG. 2 illustrates a closed loop control system according to an exemplary embodiment of the present invention for controlling the expiratory trigger sensitivity (ETS) or ratio of the measured inspiratory flow rate $V_{TI}$ to the peak inspiratory flow rate $V_{PEAK}$ at which the ventilator will switch from gas delivery to gas removal. As illustrated in the lower half of FIG. 3, during inspiration, the gas flow will gradually decay from the peak flow rate $V_{PEAK}$. In prior art ventilators, switching from gas delivery to gas removal was done at a fixed ratio of $V_{TI}/V_{PEAK}$, which resulted in expiratory asynchrony between the ventilator and patient. FIG. 2 illustrates a closed loop control system for varying the ETS or percentage of peak flow at which the inspiration phase is terminated, based on variations in a calculated patient respiratory time constant and a supra-plateau pressure.

As indicated in FIG. 2, for each pressure support breath 34, a patient respiratory time constant 36 and a supra plateau pressure 38 is measured or calculated. Based on the time constant 36, a range of ETS or $V_{TI}/V_{PEAK}$ percentage is selected at step 40. An expiratory trigger sensitivity (ETS) or $V_{TI}/V_{PEAK}$ percentage within the selected range is selected by expiratory trigger sensitivity controller 42, dependent on the measured supra-plateau pressure at step 38. The selected $V_{TI}/V_{PEAK}$ percentage is then used to control the point at which the apparatus is switched from inspiration to expiration in the next breath. When $V_{TI}/V_{PEAK}$ reaches EST, the ventilator will terminate gas delivery and switch to expiration.

Figure 5:
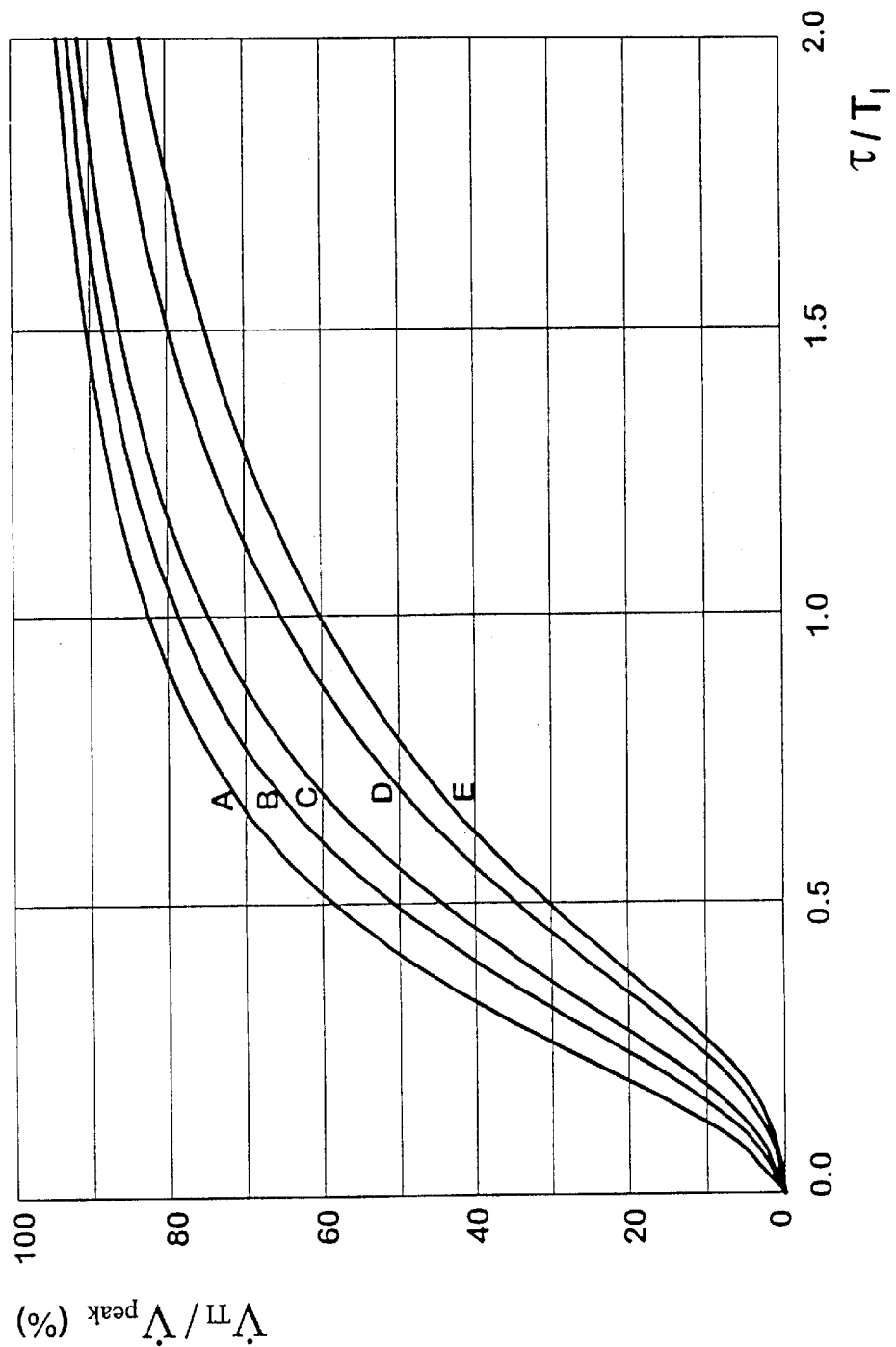
FIG. 5 illustrates the relationship of $V_{TI}/V_{PEAK}$ %, or ETS, with respiratory time constant.

Research has indicated that the expiratory trigger sensitivity that can provide a good expiratory synchrony is related to the patient respiratory time constant, as discussed in a paper entitled "Analysis of the mechanisms of expiratory asynchrony in pressure support ventilation: a mathematical approach", by Yamada, Y. and Du, H L, Journal of Applied Physiology 88; 2143–2150, 2000, the contents of which are incorporated herein by reference. FIG. 5 is a graph illustrating variation of flow at the end of inspiration to peak flow ($V_{TI}/V_{PEAK}$ %) with the ratio of the time constant τ of the respiratory system with the patient neural inspiratory time $T_I$ for different ratios of set support pressure level $P_{ps}$ with maximal patient inspiratory muscle pressure $P_{mus\ max}$. This shows that $V_{TI}/V_{PEAK}$ % rises as the respiratory time constant rises for a given $T_I$.

Figure 4:
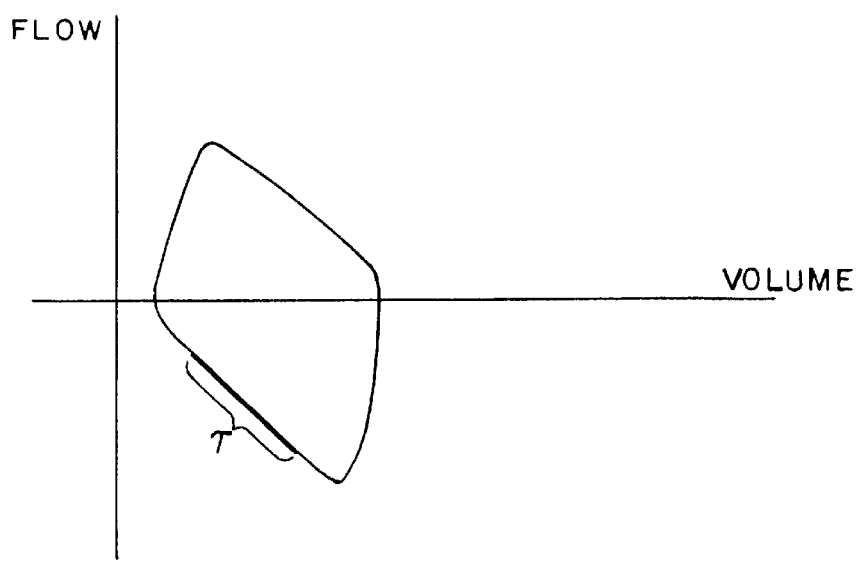
FIG. 4 illustrates a flow-volume loop for a breath cycle which may be used to calculate a patient respiratory time constant.

In the exemplary embodiment of the control system and method of this invention as illustrated in FIG. 2, the selected range of expiratory trigger sensitivity or $V_{TI}/V_{PEAK}$ % at which the inspiratory phase will be terminated is increased with increase in the patient respiratory time constant. The patient respiratory time constant is calculated for each breath by multi-linear regression, flow-volume loop, or any other valid method. FIG. 4 illustrates calculation of the respiratory time constant τ using a flow-volume loop which can be plotted for each breath. The volume is calculated by the integration of flow information from the flow sensors 26 and 28, and is then plotted against flow. The slope of the loop along line τ represents the time constant. Alternatively, the time constant may be calculated by multi-linear regression, using the relationship:

$$P = \text{Resistance } X\dot{V} + \text{Elastance } X\Delta V \quad (1)$$

Real time measurements of pressure and flow ($\dot{V}$), and volume information ($\Delta V$) can be inserted into this equation so as to obtain resistance R and elastance E. The time constant is then given by the relationship:

$$\tau = E/R \quad (2)$$

The expiratory trigger sensitivity or $V_{TI}/V_{PEAK}$ % used to control the termination of gas supply to the patient in the inspiratory phase is also varied based on the measured supra-plateau pressure for the preceding breath. The supra-plateau pressure is illustrated in the upper graph of FIG. 3, and is the pressure above the set target pressure level at the end of inspiration. The selected $V_{TI}/V_{PEAK}$ % or ETS within the range determined by the calculated τ is determined by the measured supra-plateau pressure. Generally, the higher the supra-plateau pressure, the higher the EST should be for the next breath.

Table 1 gives one example of possible ranges of $V_{TI}/V_{PEAK}$ % or ETS for different time constant ranges. However, it should be understood that these ranges are by way of example only, and that different ranges may be appropriate for different patients, dependent on physiology and general medical conditions.

TABLE 1

| Time constant | ETS or ($V_{TI}/V_{PEAK}$ %) |
|---|---|
| 0–0.8 | 10%–35% |
| 0.8–1.2 | 20%–45% |
| >1.2 | 30%–55% |

Preferably, the expiration trigger sensitivity (ETS) is increased or decreased within the determined range by 5% increments, dependent on the measured supra-plateau pressure. If the supra-plateau pressure is less than 1 cm $H_2O$, the ETS or $V_{TI}/V_{PEAK}$ % is reduced by 5%. If the supra-plateau pressure is more than 1 cm $H_2O$, the ETS or $V_{TI}/V_{PEAK}$ % is increased by 5%.

As noted above, the $V_{TI/VPEAK}$ % ranges given in Table 1 are one example of suitable settings of the expiratory trigger sensitivity or threshold based on patient respiratory time constant. However, different settings may be appropriate in other examples, based on the patient's physiology and medical condition, and the control unit may be appropriately programmed for each particular case. In general, the $V_{TI}/V_{PEAK}$ % or expiratory trigger threshold will be increased with increasing respiratory time constant, and with increase in measured supra-plateau pressure.

When the ventilator apparatus is first turned on, the expiratory trigger sensitivity controller 42 chooses a default ETS or $V_{TI}/V_{PEAK}$ %. The first breath or first few breaths of pressure support ventilation will be terminated based on the default ETS. The control unit will measure the pressure and flows from pressure gauge 30 and flow sensors 26,28 during these breaths, and will calculate the volume by integration of the flow information. The respiratory time constant is then calculated from these values, and the supra-plateau pressure at the end of each inspiration phase is also measured by pressure gauge 30. The measured time constant is used to determine the range of ETS to be used for the next breath, while the measured supra-plateau pressure determines which particular ETS within the range will be selected. A running average of two or more breaths may be used prior to any adjustment in ETS, to avoid excessive fluctuations of the calculated time constant over breaths.

Several variations in the system are possible. The pressure sensing site of pressure gauge 30 may be inside the apparatus 10 or inside the patient. The two separate flow sensors 26,28 may be replaced by a single flow sensor placed at the patient airway. Also, instead of using the supra-plateau pressure to control selection of ETS within a range, the slope of pressure change at the end of inspiration could alternatively be used. This invention may also be implemented in the dual modes, such as volume support ventilation or volume targeted pressure support ventilation. In this case, the control unit will be programmed to automatically adjust the target pressure level of the pressure support breaths within the predetermined range so that the gas volume delivered to the patient meets a set target volume.

This invention uses information from the various ventilator sensors for each pressure support breath in order to adjust the expiratory trigger sensitivity (ETS) or ratio of inspiratory flow rate to peak inspiratory flow rate at which the ventilator switches from gas delivery to gas removal for subsequent breaths, such that ventilator expiratory asynchrony is reduced or eliminated. The ETS is varied in proportion to a calculated patient respiratory time constant for one or more previous breaths, and also in proportion to a measured supra-plateau pressure or the slope of pressure change at the end of inspiration. This closed loop control of the ETS allows the respiration cycle to be updated automatically for changing patient conditions, resulting in better expiratory synchrony. Improved patient-ventilator expiratory synchrony will result in improved comfort and reduced workload to the patient, since the patient will no longer have to "fight" against the ventilator flow or waste his inspiratory muscle work. The adjustment in ETS is automatic and requires no input from the doctor or other medical personnel.

Although an exemplary embodiment of the invention has been described above by way of example only, it will be understood by those skilled in the field that modifications may be made to the disclosed embodiment without departing from the scope of the invention, which is defined by the appended claims.

We claim:

1. A pressure support ventilation system, comprising:

a ventilator unit having an input for connection to a source of breathing gases, an inspiration line for connection to a patient, a gas delivery unit for controlling gas delivery from the source to the inspiration line, an expiratory line for exhausting gases from the patient, and an expiratory unit for controlling removal of gases during expiration;

at least one flow sensor for sensing the level of gas flow in the system;

a pressure sensor for sensing pressure in the system; and a control unit connected to the gas delivery unit, expiratory unit, and the flow and pressure sensors for controlling the gas delivery and expiratory units to provide an inspiration phase in which gases are supplied to the patient through the gas delivery unit and an expiratory phase in which gases are removed from the patient;

the control unit calculating, for each breath, a patient respiratory time constant based on the outputs of the flow and pressure sensors, and including an expiratory trigger sensitivity controller for varying an expiratory trigger sensitivity in response to variations in the calculated patient respiratory time constant, such that the expiratory trigger sensitivity at which the ventilator unit switches from gas delivery to gas removal is increased with increase in the patient respiratory time constant.

2. The system as claimed in claim 1, wherein the expiratory trigger sensitivity controller includes a monitor for monitoring supra-plateau pressure at the end of each inspiration phase and for varying the expiratory trigger sensitivity in response to variations in the supra-plateau pressure, whereby the expiratory trigger sensitivity is also increased with increase in the supra-plateau pressure.

3. The system as claimed in claim 1, wherein the expiratory trigger sensitivity controller comprises a first selector for selecting a predetermined range of expiratory trigger sensitivities based on the calculated patient respiratory time constant, and a second selector for selecting a specific expiratory trigger sensitivity within the range based on the difference between a set target pressure and the actual pressure measured by the pressure sensor at the end of inspiration.

4. The system as claimed in claim 1, wherein the control unit calculates a respiratory time constant for a plurality of successive breaths, and calculates a running average time constant of the previously calculated time constants, and the expiratory trigger sensitivity controller uses the running average time constant to adjust the expiratory trigger sensitivity for the subsequent breath.

5. The system as claimed in claim 2, wherein the control unit increments the expiratory trigger sensitivity by a predetermined percentage in response to variations in the supra-plateau pressure above and below a predetermined target supra-plateau pressure.

6. The system as claimed in claim 5, wherein the predetermined percentage is 5%.

7. The system as claimed in claim 1, wherein there are a plurality of different, increasing expiratory trigger sensitivity ranges for calculated respiratory time constants within a corresponding number of different ranges.

8. A method of controlling the termination of the inhalation phase in a pressure support ventilation system, comprising the steps of:

supplying gases to a patient in a ventilator inspiration phase based on a predetermined target pressure level;

initially selecting a default expiratory trigger sensitivity at which the inspiration phase is terminated and the ventilator switches to expiration;

detecting the pressure and flow of gas during each breath, and calculating a patient respiratory time constant for that breath; and adjusting the expiratory trigger sensitivity based on the calculated respiratory time constant, such that expiratory trigger sensitivity is increased with increasing patient respiratory time constant.

9. The method as claimed in claim 8, wherein the expiratory trigger sensitivity is adjusted based on a calculated respiratory time constant for one preceding breath.

10. The method as claimed in claim 8, wherein the expiratory trigger sensitivity is adjusted based on the average of a series of calculated respiratory time constants for at least two preceding breaths.

11. The method as claimed in claim 8, including the step of measuring a supra-plateau pressure for each breath, and further adjusting the expiratory trigger sensitivity based on the measured supra-plateau pressure such that expiratory trigger sensitivity is increased with increasing supra-plateau pressure.

12. The method as claimed in claim 8, wherein the step of adjusting the expiratory trigger sensitivity comprises selecting a range of expiratory trigger sensitivities based on the calculated respiratory time constant, and selecting an expiratory trigger sensitivity within the range based on another predetermined criterion.

13. The method as claimed in claim 12, wherein a supra-plateau pressure is measured for each breath, and the selection of an expiratory trigger sensitivity within the selected range is based on the measured supra-plateau pressure.

14. The method as claimed in claim 8, including the step of storing a table comprising a series of different ranges of expiratory trigger sensitivities, each range in the table being associated with a predetermined range of respiratory time constants, and the step of adjusting the expiratory trigger sensitivity comprise looking up the ranges in the table and selecting the range associated with the calculated respiratory time constant.

15. The method as claimed in claim 8, wherein the expiratory trigger sensitivity is adjustable within a range from 10% to 55% dependent on the calculated respiratory time constant.

* * * * *